United States Patent [19]

Bedell

[11] Patent Number: 5,043,504

[45] Date of Patent: Aug. 27, 1991

[54] INHIBITION OF BUTADIENE-POLYMERIZATION DURING THE CONVERSION OF BUTADIENE TO VINYLCYCLOHEXENE

[75] Inventor: Stephen A. Bedell, Lake Jackson, Tex.

[73] Assignee: The Dow Chemical Company, Midland, Mich.

[21] Appl. No.: 578,114

[22] Filed: Sep. 5, 1990

[51] Int. Cl.$^5$ ............................................... C07C 3/42
[52] U.S. Cl. ........................................ 585/369; 585/3
[58] Field of Search ................................. 585/3, 369

[56] References Cited

U.S. PATENT DOCUMENTS

| | | | |
|---|---|---|---|
| 3,377,397 | 4/1968 | Maxfield | 585/369 |
| 3,448,129 | 6/1969 | Maxfield | 585/370 |
| 3,510,533 | 5/1970 | Maxfield | 585/369 |
| 3,523,141 | 8/1970 | Sakashita | 585/2 |
| 3,538,172 | 11/1970 | Hockmuth et al. | 585/370 |
| 3,551,467 | 12/1970 | Akakawa et al. | 585/511 |
| 3,551,507 | 12/1970 | Sakuragi et al. | 585/5 |
| 3,823,199 | 7/1974 | Wright | 585/503 |
| 3,954,665 | 5/1976 | Tkatchenk | 585/366 |
| 4,144,278 | 3/1979 | Strope | 585/508 |
| 4,181,707 | 1/1980 | Strope | 423/386 |
| 4,234,454 | 11/1980 | Strope | 502/162 |
| 4,238,301 | 12/1980 | Petit et al. | 204/59 R |
| 4,610,951 | 9/1986 | Lipson et al. | 430/313 |
| 4,973,568 | 11/1990 | Heston | 502/174 |

OTHER PUBLICATIONS

Heindirk tom Dieck et al., Chem.-Ing.-Tech 61, pp. 832–833 (1989).
W. M. Saltman, Encyclopedia of Polymer Science & Technology, vol. 2, pp. 678, 683, 684 (1965).
T. Rielly, Encyclopedia of Chemical Processing & Design, vol. 5, pp. 110, 156, 157, 164.
George Goldfinger et al., Encyclopedia of Polymer Science & Tech., vol. 7, pp. 644–647 (1965).
H. W. B. Reed, Encyclopedia of Chemical Technology, vol. 2, pp. 72–96.
D. Ballivet-Tkatchenko, Inorganica Chimica Acta, vol. 30, pp. 2-289-L290 (1978).
E. Le Roy et al., Tetrahedron Letters, vol. 27, pp. 2403–2406 (1978).
P. L. Maxfield, Inorg. Nucl. Chem. Letters vol. 6, pp. 707–711 (1970).
J. P. Candlin, et al., J. Chem. Soc. (C), pp. 1856–1860 (1968).
I. Tkatchenko, Journal of Organometal c Chemistry, vol. 124, p. C39–C42, (1977).
Gerald E. Gadd, et al., Organometallics, pp. 391–397 (1987).
A. Mortreux et al., Applied Catalysis, vol. 24, pp. 1–15 (1986).
Chemical Abstact 105:173217r(1986).
Chemical Abstract 86:107210w (1977).

*Primary Examiner*—Curtis R. Davis

[57] ABSTRACT

In a process of cyclodimerizing a conjugated diene to form a cycloalkene using a soluble iron complex as catalyst, the improvement comprises using as an inhibitor of diene polymerization, at least one hindered phenol.

15 Claims, No Drawings
}

INHIBITION OF BUTADIENE-POLYMERIZATION DURING THE CONVERSION OF BUTADIENE TO VINYLCYCLOHEXENE

BACKGROUND OF THE INVENTION

This invention relates to the production of cyclodimers of dienes, particularly to the inhibition of polymerization of the dienes during production of the cyclodimers (cyclodienes).

Such soluble iron complex catalysts as dicarbonyldinitrosyl iron Fe(NO)2(CO)2] are known to facilitate the dimerization of 1,3-butadiene to produce 4-vinylcyclohexene (VCH). This process is taught in such references as "The Catalytic Dimerization of Dienes by Nitrosylcarbonyl Transition -metal Compounds", J. P. Candlin and W. H. Janes, *J. Chem. Soc. (C).*, p. 1856 (1968), and "Catalytic Reactions Involving Butadiene. I. Selective Dimerization to 4-vinylcyclohexene With Polymetallic Precursors", 1. Tkatchenko, J. *Organometallic Chem.*, vol 124. pp. c39–c42, (1977).

A. Mortreux and F. Petit ("A New Route to Coordination Catalysis by Electrogeneration of Organometal Transition Reactive Species - A Review", *Applied Catalysis* vol 24, pp. 1–15, (1986)) have taught that the zero valent dinitrosyliron fragment, "Fe(NO)2" is central to the activity of such catalysis. They also discuss a proposed mechanism for the catalysis.

In such a dimerization processes, however, it is noted that there is also some polymerization of the diene to polydiene, e.g. butadiene to polybutadiene. The polymerization and resulting polymer not only consume starting material but also produce by-products which contaminate the vinylcyclohexene and must be removed from it. Additionally, the polymer fouls equipment. Several known inhibitors of butadiene polymerization also can react with the iron complex dimerization catalysts. Such inhibitors which are commonly used include 4-tertiary-butyl catechol (TBC) and N,N-diethylhydroxylamine (DEHA) often in combination with phenylenediamine. (see "Butadiene Polymers", chapter by W. M. Saltman in "Encyclopedia of Polymer Science and Technology", vol 2, p 683 (1965): "Butadiene, General", chapter by T. Reilly in "Encyclopedia of Chemical Processing and Design", vol 5, p 156, (1986): and Japan Patent 61,130,242 (*Chemical Abstracts* 105:173217). These inhibitors possess active hydrogens capable of being reduced by the low valent iron complexes. Such an oxidation of the iron would render the complex incapable of performing its catalytic task. In addition, the weak acid nature of such inhibitors will leave equilibrium controlled amounts of anions capable of coordinating to the iron and blocking sites of catalytic activity.

It is known to use certain hindered phenols to inhibit certain polymerizations but not polymerization of butadiene.

It would be desirable to have an inhibitor which would not react with the complex, but would inhibit the formation of polybutadiene.

Such polymer inhibition generally involves radical scavenging and chain termination, thought to involve traces of oxygen. Thus, certain compounds commonly referred to as antioxidants can function as polymerization inhibitors. One instance of such inhibitors is the use of 3,5-di-t-butyl-4-hydroxyanisole to inhibit polymerization of acrylamides. (*Chemical Abstracts* 86:107210)

SUMMARY OF THE INVENTION

In a process of cyclodimerizing a conjugated diene to form a cycloalkene using a soluble iron complex as catalyst, the improvement which comprises using as an inhibitor of diene polymerization, at least one hindered phenol.

These hindered phenols have been found to inhibit the production of polydienes while not interfering undesirably with action of the complex catalyst.

DETAILED DESCRIPTION OF THE INVENTION

The soluble iron complex catalyst is suitably any complex of zero valent iron which is an 18 valance electron complex. Determining the number of valence electrons in an iron complex is within the skill in the art, for instance as described in by F. A. Cotton and G. Wilkinson in "Advanced Inorganic Chemistry", 5th edition, p 37, Wiley Interscience, N.Y., 1988. Preferably, the soluble iron complex catalyst is one which is not undesirably inhibited by the presence of a hindered phenol. More preferably the catalyst is an iron nitrosyl complex catalyst, most preferably an iron nitrosyl catalyst such as $[Fe(NO)_2(CO)_2]$, or compounds wherein the carbonyls are replaced by olefins or diolefins $(Fe(NO)_2(X)_y$ wherein X is CO, an olefin or diolefin and y is 1 or 2 to fill the Fe valence); $[Fe(NO)_2(CO)_2]$ is most preferred for use as a catalyst in the instant invention. By soluble iron complex, it is meant that the iron complex is soluble in common organic solvents such as tetrahydrofuran, diglyme, propylene carbonate, and the like at least to a concentration sufficient to catalyze dimerization of the diene. When X is an olefin or diolefin, it preferably has from about 2 to about 12 carbon atoms, more preferably from about 4 to about 8 carbon atoms.

Preparation of soluble iron complex catalysts is within the skill in the art. For instance, Gadd, et.al. ("Photochemical Reaction of Fe(CO)2(NO)2 and Co(CO)3NO with 1,3-Butadiene in Liquid Xenon Solution: Possible Intermediates in the Catalytic Dimerization of Dienes", *Organmetallics*, vol 6, pp. 391–397, (1987)) teach that butadiene will displace the two carbonyl groups in $Fe(NO)_2(CO)_2$ to form the 18 electron species. Therefore, compounds such as $Fe(NO)_2(X)_y$, where X is a neutral ligand should be able to function as catalyst precursors, when X can be displaced by butadiene. The value of y is usually 1 or 2, so that the total number of valence electrons in the complex is 18. Ligands of this type that can be displaced by a diolefin include: carbon monoxide, phosphines (phosphine, trialkylphosphines triphenylphosphines and alkyl-phenyl phosphines), allyl and methylallyl, olefins, such as butenes (including n-butene-1, cis and trans n-butene-2, and other isomers) and VCH, and diolefins such as piperylene, butadiene and isoprene.

An alternative way of preparing the zero valent Fe(NO)2 moiety involves the chemical or electrochemical reduction of higher valent iron complexes, such as Fe(NO)2Cl or its reported dimer (Fe(NO)2Cl)2, in the presence of suitable ligands such as CO. mono and diolefins to generate an 18 electron $Fe(NO)_2(X)y$ complex. Examples of such chemical reducing agents are given in U.S. Pat. Nos. 4,234,454; 4,181,707: 4,144,278, 3,481,710: 3,377,397; 3,448,129 and 3,510,533. The last two patents along with an article by Maxfield ("The Reaction of Tetraallyltin With Transition Metal Compounds", *Inorg. Nucl. Chem. Lett.*, vol 6, pp. 707-711 (1970)) teach that when reducing agents such as tin or organotin complexes are used, the final reduced species, containing the Fe(NO)2 may be bridged to a tin complex. Electrochemical reduction is taught in U.S. Pat. No. 4,238,301 and by E. Le Roy and F. Petit, ("Cyclodimerization des Dienes Conjugues par Electrocatalyse", *Tetrahedron Letters* No. 27, pp. 2403-2406 (1978) and by D. Ballivet-Tkatchenko et al. ("The Electrochemical Reduction of (Fe(NO)$_2$Cl)$_2$. A Novel Route to the Catalytic Cyclodimerization of Diolefins.", *Inorganica Chimica Acta.* vol 30, pp. L289-L290 (1978)). Additional processes are taught in copending U.S. Ser. No. 07/348,625 filed May 8, 1989, now U.S. Pat. No. 4,973,568 (Heaton), which is incorporated by reference herein in its entirety and 07/578,110 filed Sept. 5, 1990 (Heaton), and 07/578,109 filed Sept. 5, 1990, (Heaton).

Another approach to the design of a 14 electron zero valent iron species (which will form an 18 electron species upon coordination to the reacting diolefin) is to replace the two 3 electron NO ligands with another ligand or combination of ligands that will supply a total of 6 valence electrons to the iron. Such an approach is taught by H. Tom Dieck, et. al. ("Dimerisierung von Butadien, Codimerisierung von Butadien/1-Buten and Direktverwertung des Raffinerie-C4-Schnitts an einem homogenen Eisen-Katalysator", *Chem.-Ing.-Tech.*, vol 61, pp. 832-833, (1989)) wherein a diazadiene ligand is used in place of two nitrosyl groups in the synthesis of the reduced iron catalyst.

Hindered phenols suitable for use in this invention are any compounds having an aromatic hydroxyl group which inhibit the production of polydiene in the presence of a soluble iron complex catalyst and which do not interfere undesirably with the activity of that catalyst. Preferably, the hindered phenols are those of the formula:

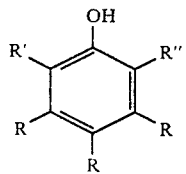

FORMULA I wherein each R is independently selected from the group hydrogen, hydroxyl, alkyl, or alkoxy groups, preferably of from 1 to 5 carbon atoms: and wherein, when any R is a hydroxyl group, that R has at least one alkyl or alkoxy group ortho to it: and R' and R" are independently selected from hydrogen, an alkyl or alkoxy group having at least 2 carbon atoms, preferably least 3 carbon atoms, more preferably R' or R" is selected from isopropyl or t-butyl groups, most preferably t-butyl groups: but wherein at least one of R' or R" is such an alkyl group of at least 2 carbon atoms. Preferably, there is no unhindered hydroxyl group on the ring, that is no hydroxyl group not having at least one group of at least 2 carbon atoms ortho to it. Most preferably, there is only one hydroxyl group on the ring. Even more preferably, at least one, preferably both, of R' and R" are t-butyl.

The R, R' and R" groups are unsubstituted or inertly substituted, that is substituted with groups which do not undesirably interfere with the inhibiting effect of the hindered phenol or catalytic activity of the soluble iron complex. Such groups include alkoxy, nitro and phenyl groups.

Suitable hindered phenols include 2,6 di-t-butylphenol, 3,5-di-isopropyl-4-hydroxy-toluene, 3,5-diisopropyl-4-hydroxyanisole and are preferably 3,5-di-t-butyl-4-hydroxy-toluene or 3,5-di-t-butyl-4-hydroxyanisole.

Such compounds are commercially available and may be prepared by methods within the skill in the art such as those described in "Alkyphenols" by H. W. B. Reed, in "Encyclopedia of Chemical Technology" vol 2, pp. 72-96, 3rd Edition, John Wiley & Sons (1978).

Any conjugated diene which can form a cyclic dimer is useful in the practice of the invention. Such dienes include butadiene, isoprene, piperylene, hexadienes and the like and are preferably piperylene. isoprene or butadiene, most preferably butadiene.

Diene streams from 10-100 weight percent can be cyclodimerized with the described iron catalyst system. The amount of catalyst needed should be enough to achieve the desired degree of butadiene conversion. This amount is dependent on reaction temperature, residence time in the reactor, concentration of butadiene and amounts of catalyst poisons such as 1,2 butadiene and acetylenes. The temperature of the reaction can be between about 50° and about 150° C. preferably between about 90° and about 130° C. The catalyst can be run with or without a solvent, with solvent to iron ratios of 0 to 1000 by weight. Solvents that can be used include diethyl ether, butyl ether, tetrahydrofuran, p-dioxane, dimethylformamide, diglyme, acetonitrile, triglyme, ethylene carbonate and propylene carbonate. Diglyme and propylene carbonate are the preferred solvents. The amount of the phenol should be selected to sufficiently inhibit polymer formation. This exact amount depends on the concentration of butadiene and the temperature, but is preferably in the range of 25 to 500 ppm in the process stream, more preferably between 50 and 250 ppm by weight.

The catalyst can be run in a once through mode or recycled and continually used over. Depending on the mode of downstream separation, the inhibitor (hindered phenol) may also be recycled back to the process, with enough fresh inhibitor added to maintain the desired concentration in the reactor section.

The following examples are given to illustrate the invention and should not be interpreted as limiting it in any way. Unless stated otherwise, all parts and percentages are given by weight. Examples (Ex.) are designated numerically while Comparative Samples (CS) which are not examples of the invention are designated alphabetically.

EXAMPLES 1-2 AND COMPARATIVE SAMPLES A AND B.

In a 300 mL autoclave is placed 0.36 g (grams) FeCl$_2$ (ferrous chloride), 0.19 g NaNO$_2$ (sodium nitrite), 0.38 g Sn (tin) powder and 18.75 g diglyme as solvent. The reactor is then flushed with CO (carbon monoxide) gas and pressured with CO to 75 psig with stirring. The temperature is maintained at 120° C. with continued stirring for 20 hours, after which, the reactor is vented and the solution filtered.

Ten (10.0) g of the solution (containing 0.15 moles/L of Fe (iron) is added to approximately 150 g of pure 1,3-butadiene at 80° C., containing the amount of inhibitor indicated in Table 1. After 10 hours, the degree of butadiene conversion is measured and is reported in the Table.

TABLE 1

| SAMPLE OR EXAMPLE | INHIBITOR | ppm inhibitor by weight | Percent conversion by moles |
|---|---|---|---|
| A | 4-t-butylcatechol | 100 | 39 |
| 1 | 3,5-di-t-butyl-4-hydroxy-toluene (BHT) | 100 | 88 |
| 2 | 3,5-di-t-butyl-4-hydroxy-anisole | 100 | 89 |
| B | None | 0 | 93 |

Examples 1-2 and Comparative Samples A and B show that 4-t-butylcatechol (Sample A) severely decreases the catalytic efficiency of $Fe(NO)_2(CO)_2$, while the hindered phenols BHT and 3,5-di-t-butyl-4-hydroxy-anisole (Examples 1 and 2, respectively) do not. Diethylhydroxylamine can not be used as an inhibitor because of formation of insoluble material with unreacted catalyst starting materials.

EXAMPLE 3

In a continuous pilot plant, consisting of two one gallon reactors in series, pure butadiene is flowed at a rate of 12 pounds per hour (lb/hr) and $Fe(CO)_2(NO)_2$ catalyst solution is flowed at 0.89 lb/hr (as a 0.5 weight percent Fe solution in diglyme). Sufficient 3,5-di-t-butyl-4-hydroxy anisole is added to maintain 300 ppm by weight in the resulting butadiene/diglyme/catalyst mixture. Reactor temperature is 75° C. No polymer formation is observed after 20 hours of runtime.

COMPARATIVE SAMPLE C

The procedure of Example 3 is repeated with no hindered phenol inhibitor. Polymer formation in control valves and circulation pumps cause plugging and pilot plant shutdown after 6 hours.

EXAMPLE 4

In a continuous pilot plant, consisting of three one-gallon reactors in series, 6 lb/hr of 65 percent by weight butadiene in crude mixture of four carbon hydrocarbons and 1.6 lb/hr of a $Fe(NO)_2(CO)_2$ solution (0.86 weight percent in Fe) in propylene carbonate are flowed continuously at temperatures between 90° and 100° C. A concentration of 3.5-di-t-butyl-4-hydroxy-anisole (hindered phenol inhibitor) is maintained at 100 ppm in the hydrocarbon/propylene carbonate mixture. After 150 hours, no evidence of polymer formation is observed.

COMPARATIVE SAMPLE D

The procedure of Example 4 is repeated except that no hindered phenol inhibitor is used. After 12 hours of operation, the pilot plant is shut down due to polymer plugging problems.

What is claimed is:

1. In a process of cyclodimerizing a conjugated diene to form a cycloalkene using a soluble iron complex as catalyst, the improvement which comprises using as an inhibitor of diene polymerization, at least one hindered phenol.

2. The process of claim 1 wherein the soluble iron complex is a zero valent, 18 valence electron complex.

3. The process of claim 2 wherein soluble iron complex is an iron nitrosyl catalyst.

4. The process of claim 3 wherein the iron nitrosyl catalyst is $Fe([C]NO)_2(X)y$ wherein X is CO, an olefin or a diolefin: and y is 1 or 2.

5. The process of claim 2 wherein the hindered phenol has a structure represented by Formula I:

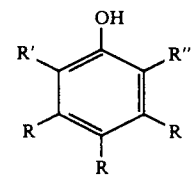

FORMULA I wherein each R is independently selected from the group hydrogen, hydroxyl, alkyl, or alkoxy groups and wherein, when any R is a hydroxyl group, that R has at least one alkyl or alkoxy group ortho to it; and R' and R" are independently selected from hydrogen, an alkyl or alkoxy group having at least 2 carbon atoms but wherein at least one of R' or R" is such an alkyl group of at least carbon atoms.

6. The process of claim 5 wherein each of R' and R" have at least 3 carbon atoms.

7. The process of claim 6 wherein each of R' and R" are isopropyl or t-butyl groups.

8. The process of claim 7 wherein each of R' and R" are t-butyl groups.

9. The process of claim 6 wherein no R is a hydroxyl group.

10. The process of claim 9 wherein the hindered phenol is 3,5-di-t-butyl-4-hydroxyanisole.

11. The process of claim 9 wherein the hindered phenol is 3,5-di-t-butyl-4-hydroxytoluene.

12. The process of claim 5 wherein the diene is piperylene, isoprene or butadiene.

13. The process of claim 10 wherein the diene is butadiene.

14. The process of claim 1 where said conjugated diolefin is butadiene, the iron complex is $Fe(CO)_2(NO)_2$ or compounds formed from $Fe(CO)_2(NO)_2$ by substitution of the carbonyls with olefins or diolefins in a process stream, and the hindered phenol is 3,5-t-butyl-4-hydroxyanisole.

15. The process of claim 14 wherein the olefin or diolefin on the iron complex is at least one butene, vinylcyclohexene, piperylene, butadiene or isoprene.

* * * * *